United States Patent
Puckett

(10) Patent No.: US 10,685,390 B1
(45) Date of Patent: Jun. 16, 2020

(54) OPTIMIZED DRUG SUPPLY LOGISTICAL TECHNIQUES FOR A CENTRAL DRUG DISTRIBUTION CENTER

(71) Applicant: Verity Solutions, Kirkland, WA (US)

(72) Inventor: George Puckett, Kirkland, WA (US)

(73) Assignee: Verity Solutions, Kirkland, WA (US)

(*) Notice: Subject to any disclaimer, the term of this patent is extended or adjusted under 35 U.S.C. 154(b) by 0 days.

(21) Appl. No.: 16/428,266

(22) Filed: May 31, 2019

Related U.S. Application Data

(63) Continuation of application No. 16/178,446, filed on Nov. 1, 2018, now abandoned.

(51) Int. Cl.
*G16H 40/20* (2018.01)
*G06Q 30/06* (2012.01)
*G16H 20/10* (2018.01)

(52) U.S. Cl.
CPC ......... *G06Q 30/0635* (2013.01); *G16H 20/10* (2018.01)

(58) Field of Classification Search
CPC .............................. G16H 20/10; G16H 40/20
See application file for complete search history.

(56) References Cited

U.S. PATENT DOCUMENTS

| | | | | |
|---|---|---|---|---|
| 2001/0004734 A1* | 6/2001 | Kudoh | ............. | G06Q 30/06 705/26.41 |
| 2004/0230502 A1 | 11/2004 | Fiacco et al. | | |
| 2009/0254412 A1 | 10/2009 | Braswell et al. | | |
| 2011/0251850 A1 | 10/2011 | Stephens | | |
| 2012/0030070 A1 | 2/2012 | Keller et al. | | |
| 2015/0332422 A1 | 11/2015 | Gilmartin | | |
| 2016/0042147 A1* | 2/2016 | Maurer | ............. | G06Q 50/24 705/3 |
| 2019/0147994 A1* | 5/2019 | Hassad | ............. | G16H 20/10 |

OTHER PUBLICATIONS

"Average Wholesale Price (AWP) as a Pricing Benchmark"; L. Anderson; Aug. 16, 2018 (Year: 2018).*

* cited by examiner

*Primary Examiner* — John A Pauls
(74) *Attorney, Agent, or Firm* — Perkins Coie LLP

(57) ABSTRACT

A facility for managing distribution of a drug is described. The facility generates an order for the drug on behalf of one or more purchasing hospitals, the order specifying each purchasing hospitals' identity and a quantity of the drug ordered on its behalf. The facility selects the specified identities of the purchasing hospitals and the specified quantities of the drug in a manner that takes advantage of opportunities that one or more distinguished hospitals among the purchasing hospitals have to order the drug at a discounted price. The facility reimburses each purchasing hospital for the drug ordered on its behalf at an undiscounted price. The facility causes the ordered quality of the drug to be physically distributed to one or more consuming hospitals, and causes each consuming hospital to be charged for the distributed quantity of the drug at the undiscounted price.

8 Claims, 15 Drawing Sheets

| drug | seller | container size | price level | price per dose | |
|---|---|---|---|---|---|
| Amoxicillin | A | 50 | GPO | $5.85 | ← 311 |
| Amoxicillin | A | 50 | WAC | $11.50 | ← 312 |
| Amoxicillin | A | 50 | 340B | $4.90 | ← 313 |
| Amoxicillin | B | 50 | GPO | $6.90 | ← 314 |
| Amoxicillin | B | 50 | WAC | $12.10 | ← 315 |
| Amoxicillin | B | 50 | 340B | $5.20 | ← 316 |
| Amoxicillin | C | 50 | GPO | $7.15 | ← 317 |
| Amoxicillin | C | 50 | WAC | $13.15 | ← 318 |
| Amoxicillin | C | 50 | 340B | $6.60 | ← 319 |
| Amoxicillin | A | 100 | GPO | $6.85 | ← 320 |
| ... | | | | | |
| Ibuprofen | A | 50 | GPO | $1.50 | ← 321 |
| ... | | | | | | drug price schedule — 300

FIG. 4 dispense table — 400

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | |
| 10/10/2019 | 16:19:21 | 331A | 111-55-8888 | inpatient | Amoxicillin | |
| 10/10/2019 | 22:01:33 | 222C | 777-33-9999 | outpatient | Amoxicillin | |
| 10/10/2019 | 22:12:22 | 301A | 111-55-8888 | inpatient | Amoxicillin | |
| ... | | | | | | |

401  402  403  404  405  406  407

411  412  413  414  415  416

| drug | inpatient or outpatient | count of unapplied dispenses |
|---|---|---|
| Amoxicillin | inpatient | 63 |
| Amoxicillin | outpatient | 44 |
| Ibuprofen | inpatient | 7 |
| ... | | | unapplied dispense tally table — 500
511, 512, 513
501, 502, 503

*FIG. 5*

FIG. 6 drug purchase table — 600

| purchase ID | date | price level | drug | seller | container size |
|---|---|---|---|---|---|
| 983991 | 4/4/2017 | WAC | Amoxicillin | B | 50 |

FIG. 7 drug purchase table — 700

| purchase ID | date | price level | drug | seller | container size |
|---|---|---|---|---|---|
| 983991 | 4/4/2017 | WAC | Amoxicillin | B | 50 |
| 991001 | 10/11/2019 | GPO | Amoxicillin | A | 50 |

FIG. 8 dispense table 800

| date 801 | time 802 | location 803 | patient 804 | inpatient or outpatient 805 | drug 806 | purchase ID of purchase to which applied 807 |
|---|---|---|---|---|---|---|
| 10/10/2019 | 15:54:03 | 407A | 444-11-3333 | outpatient | Amoxicillin | 983991 (811) |
| 10/10/2019 | 15:54:07 | 106B | 444-22-9999 | inpatient | Ibuprofen | (812) |
| 10/10/2019 | 15:59:31 | 331A | 555-11-8888 | outpatient | Amoxicillin | (813) |
| 10/10/2019 | 16:19:21 | 331A | 111-55-8888 | inpatient | Amoxicillin | 991001 (814) |
| 10/10/2019 | 22:01:33 | 222C | 777-33-9999 | outpatient | Amoxicillin | (815) |
| 10/10/2019 | 22:12:22 | 301A | 111-55-8888 | inpatient | Amoxicillin | 991001 (816) |
| ... | | | | | | |

FIG. 9

| drug | inpatient or outpatient | count of unapplied dispenses |
|---|---|---|
| Amoxicillin | inpatient | 13 |
| Amoxicillin | outpatient | 44 |
| Ibuprofen | inpatient | 7 |
| ... | | | unapplied dispense tally table — 900
901, 902, 903
911, 912, 913

FIG. 10 dispense table — 1000

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | |
| 10/10/2019 | 16:19:21 | 331A | 111-55-8888 | inpatient | Amoxicillin | 991001 |
| 10/10/2019 | 22:01:33 | 222C | 777-33-9999 | outpatient | Amoxicillin | |
| 10/10/2019 | 22:12:22 | 301A | 111-55-8888 | inpatient | Amoxicillin | 991001 |
| 10/11/2019 | 5:11:12 | 301A | 111-55-8888 | inpatient | Amoxicillin | |
| 10/11/2019 | 5:31:02 | 110 | 888-00-1111 | outpatient | Amoxicillin | |
| ... | | | | | | |

1001, 1002, 1003, 1004, 1005, 1006, 1007

1011, 1012, 1013, 1014, 1015, 1016, 1017, 1018

FIG. 11 unapplied dispense tally table — 1100

| drug | inpatient or outpatient | count of unapplied dispenses |
|---|---|---|
| Amoxicillin | inpatient | 51 |
| Amoxicillin | outpatient | 60 |
| Ibuprofen | inpatient | 21 |
| ... | | |

FIG. 12 drug purchase table — 1200

| purchase ID | date | price level | drug | seller | container size |
|---|---|---|---|---|---|
| 983991 | 4/4/2017 | WAC | Amoxicillin | B | 50 |
| 991001 | 10/11/2019 | GPO | Amoxicillin | A | 50 |
| 991340 | 10/12/2019 | 340B | Amoxicillin | B | 50 |

*FIG. 13* dispense table — 1300

| date | time | location | patient | inpatient or outpatient | drug | purchase ID of purchase to which applied |
|---|---|---|---|---|---|---|
| 10/10/2019 | 15:54:03 | 407A | 444-11-3333 | outpatient | Amoxicillin | 983991 |
| 10/10/2019 | 15:54:07 | 106B | 444-22-9999 | inpatient | Ibuprofen | |
| 10/10/2019 | 15:59:31 | 331A | 555-11-8888 | outpatient | Amoxicillin | 991340 |
| 10/10/2019 | 16:19:21 | 331A | 111-55-8888 | inpatient | Amoxicillin | 991001 |
| 10/10/2019 | 22:01:33 | 222C | 777-33-9999 | outpatient | Amoxicillin | 991340 |
| 10/10/2019 | 22:12:22 | 301A | 111-55-8888 | inpatient | Amoxicillin | 991001 |
| 10/11/2019 | 5:11:12 | 301A | 111-55-8888 | inpatient | Amoxicillin | |
| 10/11/2019 | 5:31:02 | 110 | 888-00-1111 | outpatient | Amoxicillin | 991340 |
| ... | | | | | | |

| drug | inpatient or outpatient | count of unapplied dispenses |
|---|---|---|
| Amoxicillin | inpatient | 51 |
| Amoxicillin | outpatient | 10 |
| Ibuprofen | inpatient | 21 |
| ... | | | unapplied dispense tally table 1400
1401 / 1402 / 1403
1411: 51, 1412: 10, 1413: 21

OPTIMIZED DRUG SUPPLY LOGISTICAL TECHNIQUES FOR A CENTRAL DRUG DISTRIBUTION CENTER

BACKGROUND

Hospitals and other kinds of healthcare facilities dispense drugs to patients. The healthcare facilities generally purchase these drugs from suppliers.

In some cases, drugs purchased by healthcare facilities from suppliers are routed through a Central Drug Distribution Center ("CDC"). A typical CDC receives drugs on behalf of multiple "member health care facilities;" repackages them in individual doses; and distributes the drugs in individual dose form to particular member healthcare facilities.

While CDCs are in some cases commonly owned with all of their member healthcare facilities, in other cases, not all of the member healthcare facilities are co-owned with the CDC.

BRIEF DESCRIPTION OF THE DRAWINGS

FIGS. 3-14 are data structure diagrams showing sample contents of tables used by the facility in some embodiments.

DETAILED DESCRIPTION

Figure 1:
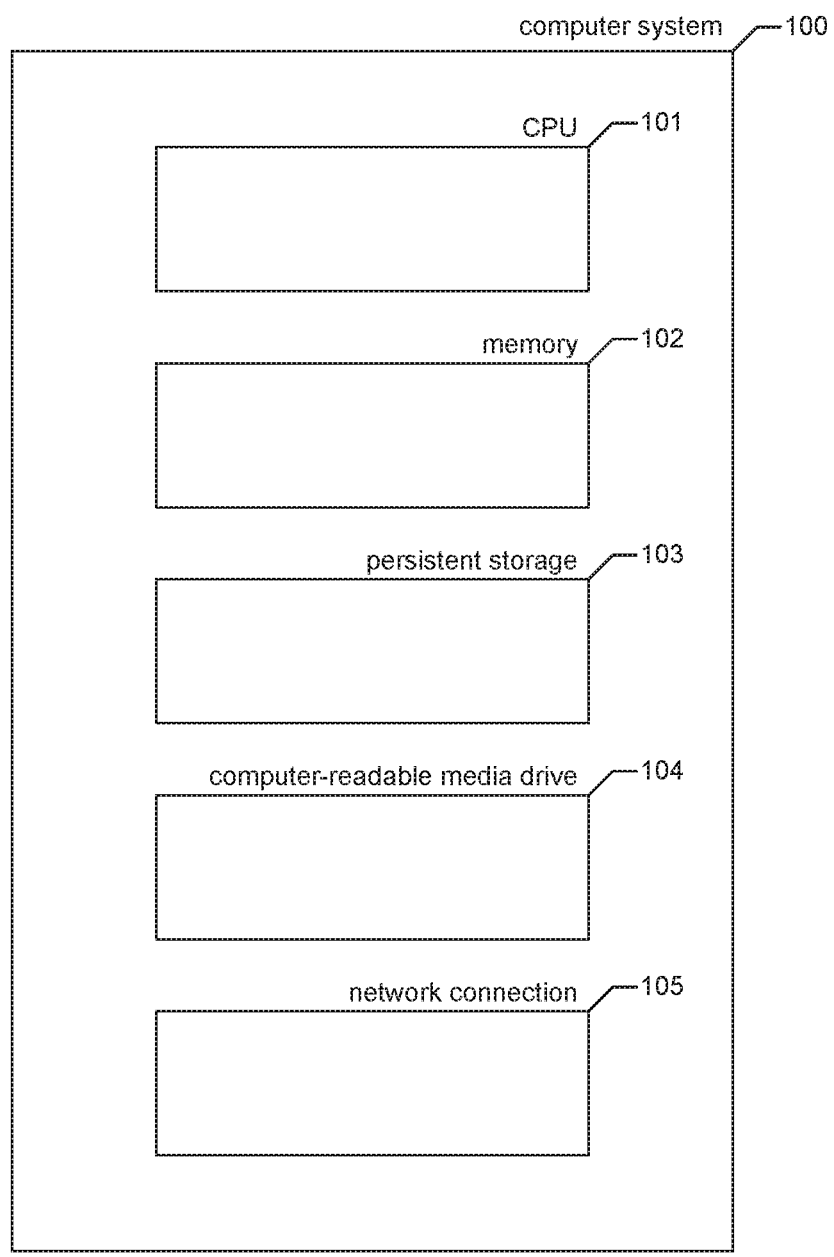
FIG. 1 is a block diagram showing some of the components typically incorporated in at least some of the computer systems and other devices on which the facility operates.

Section 340B of the Public Health Service Act provides a discounted drug pricing program that applies to certain purchases of drugs by certain healthcare facilities ("enrolled entities"). For efficiency's sake, enrolled entity healthcare facilities of all types are sometimes referred to herein as "hospitals."

Under section 340B, an enrolled entity must order drugs separately for patients treated as inpatients and patients treated as outpatients. For patients treated as inpatients, the enrolled entity typically always orders at a discounted price for inpatients, called "GPO" (Group Purchasing Organization price). For patients treated as outpatients, the enrolled entity first orders a particular drug from a particular seller at a retail price called "WAC" (Wholesale Acquisition Cost). The enrolled entity can subsequently REORDER the same drug from the same seller at a discounted 340B price. In order to perform this reorder of a container of drugs at 340B price, the enrolled entity must be able to show that (1) it previously purchased the same-sized container from the same seller at WAC; and (2) it has dispensed all of the doses contained by a container of that size to outpatients. At enrolled entities that commingle drugs they purchase for inpatients at GPO with drugs they purchase for outpatients at WAC and 340B price, any meaningful attempt at 340B compliance must involve strict accounting for drugs dispensed to inpatients versus outpatients.

To satisfy the requirement that an enrolled entity be able to, for a container of a drug reordered at 340B price, account for the dispenses of all of the doses in the container to outpatients, conventional compliance systems attribute each administration of a dose of a drug (a "dispense") to an inpatient as soon as it occurs to a particular combination of the drug with a container size and a seller from whom the drug was purchased in that container size. When a hospital seeks to order a drug in a particular container size from a particular seller, conventional systems count the doses dispensed to outpatients attributed to the combination of the drug, container size, and seller, to see if they add up to the number of doses in the container size; only if they do does a conventional system allow the purchase to proceed as a reorder at 340B price; otherwise, a conventional system performs the order at the more expensive WAC price.

The inventors have recognized a number of disadvantages with the approach employed by conventional systems. First, for any given dispensed dose, it can be difficult to identify the combination of container size and seller to which to attribute the dispense, costing the conventional system significant processing resources. Second, in some cases, the complex logic needed to attribute a dispense to a combination of container size and seller may fail, depriving the healthcare facility of any pricing benefit from the outpatient dispense. Third, the conventional approach often unnecessarily extends the healthcare facility's purchase of drugs at higher WAC prices that could instead be purchased at lower 340B prices.

Additional disadvantages of conventional approaches recognized by the inventors relate to the operation of CDCs. In particular, the inventors have noted that conventional ordering by CDCs is often done manually, with no particular emphasis on or ability to achieve pricing advantages.

In order to overcome these disadvantages of conventional systems, the inventors have conceived and reduced to practice a software and/or hardware facility for ordering drugs using late attribution and price optimization, including price optimization for orders placed by a CDC ("the facility").

The facility responds to a dispense to an inpatient by incrementing a counter not associated with any particular container size or seller, but only with the drug. At the time of ordering a new container of a drug of a particular size from a particular seller, the facility checks to see (1) whether the hospital previously ordered a container of that drug of that size from the same seller, and (2) whether the number of dispensed doses in this much broader counter is as least as great as the number that fits in the container. If so, the facility allows the drug to be ordered at 340B price, only then attributing a set of unattributed outpatient dispenses whose number matches the size of the container to the order, which has a particular combination of container size and seller.

In some embodiments, rather than specifying the seller from which it wants to buy a drug, the hospital simply specifies the drug and container size it wants. The facility automatically identifies a seller to order it from based upon (a) current price schedules from all sellers at all price levels, (b) the sellers from which containers of the drug have been previously purchased, and (c) the number of doses of the drug dispensed to inpatients that haven't already been used as the basis for a 340B order.

In some embodiments, the hospital specifies the drug and number of doses it wants, to the exclusion of container size.

In response, the facility automatically chooses both seller and container size(s) in a way that optimizes average price paid per dose.

In some embodiments, the facility makes ordering recommendations and/or decisions for a CDC serving several member hospitals. When an order for a drug is being placed by the CDC, the invention accesses (1) records of containers of the drug purchased by each member hospital and shipped to the CDC to see from which sellers, for which hospitals, orders have previously been placed, and (2) inpatient and outpatient dispense records of the member hospitals. The facility then allocates portions of the order across the member hospitals in a way that optimizes the average price paid.

In cases where the CDC and member hospitals are not all owned by the same entity, for drugs purchased at the 340B price: (1) for each container of the drug ordered on behalf of the hospital, the hospital pays the 340B price to the seller; (2) for each container of the drug ordered on behalf of the hospital, the CDC pays the higher WAC price to the hospital; and (3) for any containers of the drug supplied by the CDC to the hospital (which may be greater or less than the number of containers ordered on behalf of the hospital), the hospital pays the CDC the WAC price. In some embodiments, the price paid to the CDC by the hospital is a markup over WAC to compensate the CDC for its work/expenses on behalf of the hospital. In some embodiments, the CDC is compensated by the member hospitals for its services in one or more of a variety of other ways.

By performing in some or all of the ways described above, the facility achieves one or more of the following, both with respect to individual hospitals and groups of hospitals serviced by a CDC: (1) simplifies the process of dispense attribution, such that it consumes lower levels of processing and storage resources, permitting it to be executed on less powerful and less expensive hardware resources and/or permitting it to execute using lower levels of cloud computing and storage resources; (2) does not discard the pricing benefit of any outpatient dispense; and/or (3) on average accelerates the opportunity to purchase drugs at lower 340B prices.

FIG. 1 is a block diagram showing some of the components typically incorporated in at least some of the computer systems and other devices on which the facility operates. In various embodiments, these computer systems and other devices 100 can include server computer systems, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") 101 for executing computer programs; a computer memory 102 for storing programs and data while they are being used, including the facility and associated data, an operating system including a kernel, and device drivers; a persistent storage device 103, such as a hard drive or flash drive for persistently storing programs and data; a computer-readable media drive 104, such as a floppy, CD-ROM, or DVD drive, for reading programs and data stored on a computer-readable medium; and a network connection 105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 2:
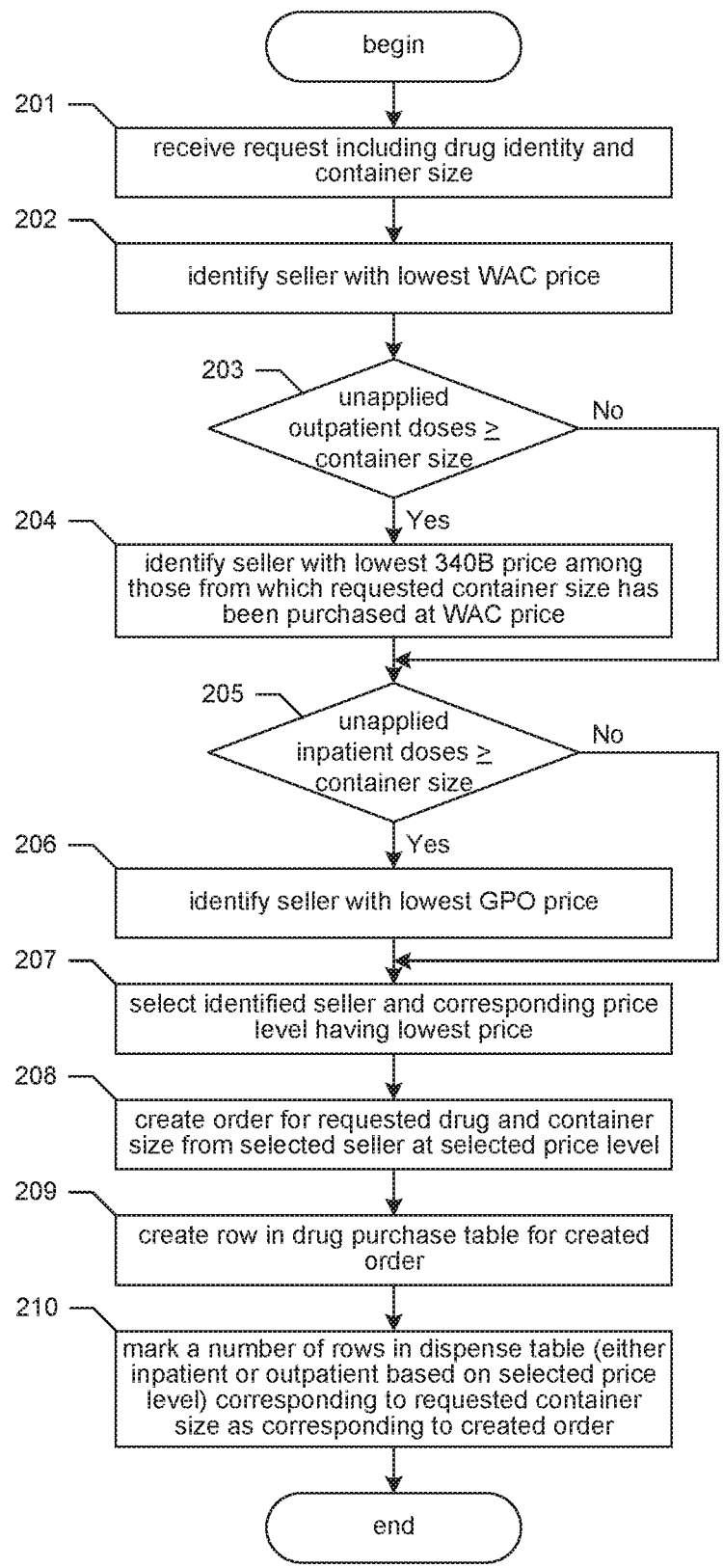
FIG. 2 is a flow diagram showing a process performed by the facility in some embodiments in order to handle a drug ordering request for a hospital.

FIG. 2 is a flow diagram showing a process performed by the facility in some embodiments in order to handle a drug ordering request on behalf of a subject hospital. In act 201, the facility receives a request that includes the identity of a drug to be ordered on behalf of a subject hospital and a container size. In various embodiments, the request identifies the drug in one or more various ways, including: chemical identity; form, such as tablet, capsule, drink, injection, aerosol, etc.; manufacturer and/or brand-name; and/or encoded identifiers conveying this or other information. In an example, the facility receives a first request to purchase a 50-dose container of the drug Amoxicillin. In act 202, the facility identifies the seller having the lowest WAC price. FIG. 3 is a table diagram showing sample contents of a drug price schedule table. The drug price schedule table contains current pricing information for drugs available from different sellers at different price levels. In various embodiments, the drug price schedule table is updated at regular intervals; in response to notifications from sellers; in response to each attempt to read it; etc. Each row of the drug price schedule table 300, such as shown rows 311-321, corresponds to a different combination of a drug, a seller, a container size, and a price level. Each row is divided into the following columns: a drug column 301 identifying the drug to which the row corresponds; a seller column 302 identifying a seller to whom the row corresponds; a container size column 303 showing the number of doses contained by a container to which the row corresponds; a price level column 304 identifying the pricing program to which the row corresponds; and a price per dose column 305 indicating the price per dose to order the drug from the seller in the specified container size at the specified price level. For example, row 311 indicates that the drug Amoxicillin can be ordered from seller A in a container holding 50 doses at the GPO price level for $5.85 a dose.

While FIG. 3 and each of the table diagrams discussed below show a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed and/or encrypted; may contain a much larger number of rows than shown; etc.

The drug price schedule 300 shown in FIG. 3 contains WAC prices for Amoxicillin in rows 312, 315, and 318. By comparing these, the facility determines that the lowest WAC price is $11.50 for seller A shown in row 312. Accordingly, in act 203, the facility identifies seller A.

In act 203, if the number of unapplied outpatient doses of this drug is greater than or equal to the requested container size, then the facility continues in act 204, else the facility continues in act 205. In some embodiments, the facility performs the comparison of act 203 using contents of a dispense table and/or an unapplied dispense tally table, shown in FIGS. 4 and 5 and discussed below.

FIG. 4 is a table diagram showing sample contents of a dispense table at a first time. The dispense table 400 is made up of rows, such as shown rows 411-416, each corresponding to an instance in which a dose of a drug was administered to a patient by the subject hospital. Each row is divided into the following columns: a date column 401 indicating the date on which the drug was dispensed; a time column 402 indicating a time at which the drug was dispensed; a location column 403 indicating a physical location at which the drug was dispensed; a patient column 404 containing an identifier of the patient to whom the drug was dispensed; an inpatient or outpatient column 405 indicating whether the drug was dispensed to the patient as an inpatient or as an outpatient; a drug column 406 identifying the dispensed drug; and a purchase ID of purchase to which applied column 407, identifying a purchase of the dispensed drug that occurred after the dispense that was made to replace the dose of the drug given to the patient in the dispense to which the row corresponds. For example, row 411 indicates that, at 3:54:03 PM on Oct. 10, 2019, a patient having the identifier 44-11-3333 was given the drug Amoxicillin in location 407A as an outpatient, and that this dispense was later used as a basis for repurchasing Amoxicillin in a purchase having purchase ID 983991.

In some embodiments, the comparison of act 203 is performed based upon a query performed against the dispense table that counts the number of rows of the dispense table having "outpatient" in the inpatient or outpatient column 405, having "Amoxicillin" in the drug column 406, and having no purchase ID in the purchase ID of purchase to which applied column 407. Across rows 411-416 of dispense table 400 shown in FIG. 4, this query would return the result "2"; across all of the rows of dispense table 400, including those not shown in FIG. 4, the result may be larger.

FIG. 5 is a table diagram showing sample contents of an unapplied dispense tally table at the first time. The unapplied dispense tally table is based on the dispense table and summarizes the dispense table in a way that is useful in performing act 203. In various embodiments, the unapplied dispense tally table is updated in response to each change to the dispense table; re-created from the dispense table at regular intervals; re-created from the dispense table in response to each attempt to read the unapplied dispense tally table; etc.

The unapplied dispense tally table 500 is made up of rows, such as shown rows 511-513, each corresponding to a different combination of drug with inpatient or outpatient patient status. Each row is divided into the following columns: a drug column 501 identifying a drug that has been dispensed by the subject hospital; an inpatient or outpatient column 502 indicating whether the row is included in the unapplied dispense tally table to count dispenses to inpatients or dispenses to outpatients; and a count of unapplied dispenses column 503 indicating the number of dispenses of the drug to which the row corresponds that have been performed to patients having the status to which the row corresponds and have not been used as a basis for reordering that drug. For example, row 511 indicates that 63 doses of Amoxicillin have been administered to inpatients and not subsequently used as a basis for reordering Amoxicillin.

In the example represented by the contents of the dispense table and unapplied dispense tally table shown in FIGS. 4 and 5, only 44 doses of Amoxicillin have been administered to outpatients and not used as a basis to reorder Amoxicillin (see row 412 of unapplied dispense tally table 500), which is less than the 50-dose container size specified by the first purchase request. Accordingly, the facility continues in act 205.

Returning to FIG. 2, in act 205, if the number of unapplied inpatient doses is greater than or equal to the requested container size, then the facility continues in act 206, else the facility continues in act 207. In a manner similar to that described above in connection with act 203, the facility performs the comparison of act 205 based on the contents of the dispense table and/or the unapplied dispense tally table. In this case, 63 doses of Amoxicillin have been administered to inpatients and not used as a basis to reorder Amoxicillin (see row 511 of unapplied dispense tally table 500), which is greater than or equal to the 50-dose container size specified by the first purchase request. Accordingly, the facility continues in act 206.

In act 206, the facility identifies the seller having the lowest GPO price. In some embodiments, the facility uses a drug price schedule table to perform the identification of act 206. By comparing the contents of the price per dose column for rows 311, 314, and 317 of drug price schedule table 300, the facility identifies seller as having the lowest GPO price for Amoxicillin in a 50-dose container.

Returning to FIG. 2, in act 207, the facility selects the identified seller and identified the corresponding price level having the lowest price. For the first purchase request, two combinations of seller and price level are identified: (1) seller A and the WAC price level $11.50 identified in act 202, and (2) seller A and the GPO price level $5.85 identified in act 206. In act 207, the facility selects the lower of these, seller A and the GPO price level. In act 208, the facility creates an order for the requested drug, here Amoxicillin, and requested container size, here 50 doses, from the selected seller, seller A, at the selected price level, the GPO price level. In various embodiments, the facility communicates the order to the seller in a variety of ways, such as by calling an API exposed by the seller; sending an email or fax to the seller; automatically interacting with a web interface exposed by the seller; etc. In act 209, the facility creates a row in a drug purchase table for the created order.

FIGS. 6-7 show the creation of a row in the drug purchase table for the created order. FIG. 6 is a table diagram showing sample contents of the drug purchase table at the first time. The drug purchase table 600 is made up of rows, such as shown row 611, each corresponding to a different purchase of a drug by the subject hospital. Each row is divided into the following columns: a purchase ID column 601 unique identifying the purchase; a date column 602 identifying the date on which the purchase occurred; a price level column 603 identifying the prep price level at which the purchase was made; a drug column 604 identifying the drug purchased; a seller column 605 identifying the seller from which the drug was purchased; and a container size column 606 indicating the size of the purchase container of the drug. For example, row 611 indicates that the purchase having purchase ID 983991 was performed on Apr. 4, 2017 from seller B, purchasing a 50-dose container of Amoxicillin at the WAC price level.

FIG. 7 is a table diagram showing sample contents of the drug purchase table at a second time later than the first time, after the drug purchase table has been updated in response to the purchase for the first request. By comparing drug purchase table 700 shown in FIG. 7 to drug purchase table 600 shown in FIG. 6, it can be seen that the facility has added row 712, which corresponds to the purchase for the first request. In particular, row 712 indicates that the purchase having purchase ID 991001 was performed on Oct. 11, 2019 from seller A, purchasing a 50-dose container of Amoxicillin at the GPO price level.

Returning to FIG. 2, in act 210, the facility marks a number of rows of the dispense table that corresponds to the requested container size as corresponding to the order created in act 208.

FIG. 8 is a table diagram showing sample contents of the dispense table at the second time, after it has been updated by the facility in act 210. By comparing dispense table 800 shown in FIG. 8 is dispense table 300 shown in FIG. 4, it can be seen that the facility has added purchase ID 991001 to rows 814 and 816, each corresponding to a dispense of the drug Amoxicillin to a patient as an inpatient. Act 210 also involves adding this purchase ID to 48 other rows each corresponding to a dispense of the drug Amoxicillin to a patient as an inpatient, not shown in FIG. 8.

In some embodiments, this modification to the dispense table automatically updates the unapplied dispense tally table to reduce the count of unapplied dispenses column for the appropriate row by the size of the purchase container. In some embodiments, the facility explicitly updates the unapplied dispense tally table to perform this reduction (not shown in FIG. 2).

FIG. 9 is a table diagram showing sample contents of the unapplied dispense tally table at the second time, after it has been updated to reflect changes to the dispense table based upon the purchase performed in response to the first request. By comparing unapplied dispense tally table 900 shown in FIG. 9 to unapplied dispense tally table 400 shown in FIG. 5, it can be seen that the facility has, in row 911, reduced the count of unapplied dispenses to inpatients of Amoxicillin by the size of the purchase container—50 doses—from 63 to 13.

Continuing the example, in a second purchase request received at a third time, the purchase of another 50-dose container of Amoxicillin is requested. FIGS. 10 and 11 show the contents of the dispense table and the unapplied dispense tally table at this third time when the second purchase request is received. By comparing the dispense table 1000 shown in FIG. 10 to dispense table 800 shown in FIG. 8, it can be seen that additional dispenses of the drug Amoxicillin have been performed, as shown for example in new rows 1017 and 1018 of dispense table 1000. By comparing the unapplied dispense tally table 1100 shown in FIG. 11 to unapplied dispense tally table 900 shown in FIG. 9, it can be seen that the count of unapplied inpatient dispenses of Amoxicillin is now 51, and the count of unapplied outpatient dispenses of Amoxicillin is now 60.

In performing the process shown in FIG. 2 for the second purchase request: In act 202, the facility identifies the seller having the lowest WAC price. The drug price schedule 300 shown in FIG. 3 contains WAC prices for Amoxicillin in rows 312, 315, and 318. By comparing these, the facility determines that the lowest WAC price is $11.50 for seller A shown in row 312. Accordingly, in act 203, the facility identifies seller A as having the lowest WAC price. (While in some circumstances the drug price schedule table may have changed from the version shown in FIG. 3, for efficiency's sake, here the drug price schedule table is treated as if it has not changed.)

In act 203, the facility determines that the number of unapplied outpatient doses, 60, is greater than or equal to the requested container size, 50; accordingly, the facility continues from act 203 to act 204. In act 204, the facility identifies the seller having the lowest 340B price among those sellers from which the requested container size has been purchased at the WAC price level. The drug price schedule 300 shown throughout in FIG. 3 contains 340B prices for Amoxicillin in rows 313, 316, and 319. The 340B price for Amoxicillin shown in row 313 for seller A, $4.90, is lower than the 340B price for Amoxicillin from the other two sellers. However, the drug purchase table 700 shown in FIG. 7 does not contain a row indicating that a 50-dose container of Amoxicillin has been purchased from seller A at the WAC price level. Accordingly, the facility selects the next-the higher 340B price, $5.20 from seller B, shown in row 316. As contrasted with seller A, the drug purchase table 700 does contain a row—row 711—indicating that a 50-dose container of Amoxicillin was purchased from seller B at the WAC price level.

After act 204, in processing the second purchase request, the facility in act 205 determines that the number of unapplied inpatient doses, 51, is greater than the container size, and thus continues in act 206. In act 206, the facility identifies as the seller with the lowest GPO price seller A, shown by row 311 of the drug price schedule table 300 to sell Amoxicillin at a price of $5.85 at the GPO price level.

For the second purchase request, in act 207, the facility selects among the following: WAC price of $11.50 from seller A; 340B price of $5.20 from seller B; and GPO price of $5.85 from seller A. In particular, the facility selects the 340B price of $5.20 from seller B.

FIG. 12 is a data structure diagram showing sample contents of the drug purchase table at a fourth time that reflect the purchase of a 50-dose container of Amoxicillin from seller B at the 340B price level in response to the second purchase request in accordance with act 209. It can be seen by comparing drug purchase table 1200 shown in FIG. 12 to drug purchase table 700 shown in FIG. 7 that the facility has added row 1213, which identifies this purchase using purchase ID 991340.

FIG. 13 is a data structure diagram showing sample contents of the dispense table at the fourth time in accordance with act 210. It can be seen by comparing dispense table 1300 shown in FIG. 13 to dispense table 1000 shown in FIG. 10 that the facility is added new purchase ID 991340 to rows 1313, 1315, and 1318 for outpatient dispenses of Amoxicillin. The facility has similarly added this new purchase ID 47 to other rows for outpatient dispenses of Amoxicillin, not shown in FIG. 13.

FIG. 14 is a data structure diagram showing sample contents of the unapplied dispense tally table to reflect the purchase in response to the second request. By comparing unapplied dispense tally table 1400 shown in FIG. 14 to unapplied dispense tally table 1100 shown in FIG. 11, it can be seen that the count of unapplied outpatient Amoxicillin dispenses has been reduced by the size of the purchase container, 50, from 60 to 10.

Those skilled in the art will appreciate that the acts shown in FIG. 2 may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 15:
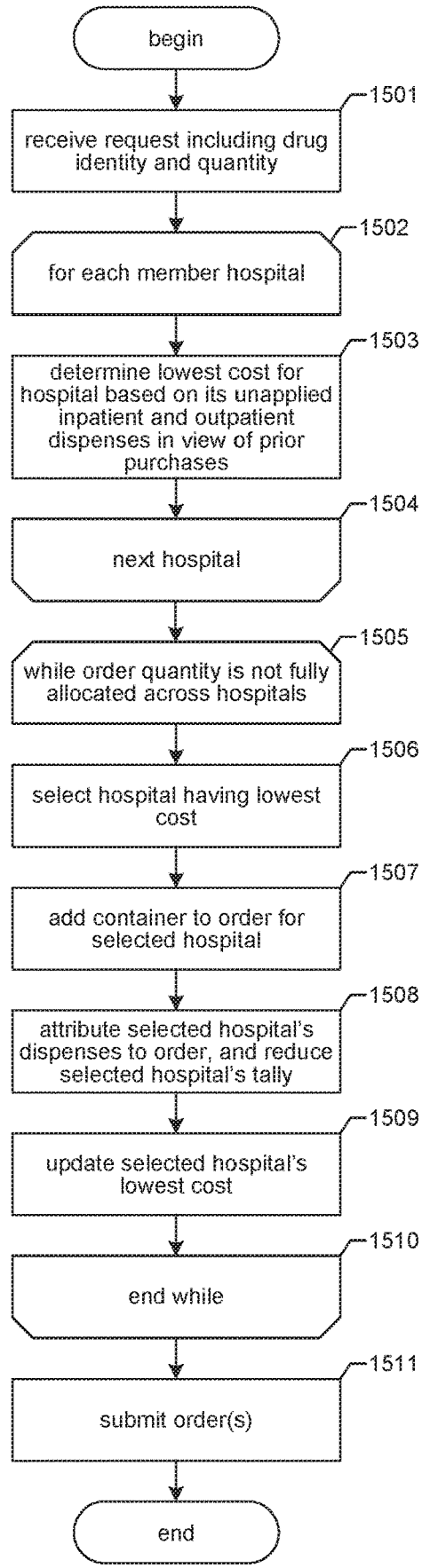
FIG. 15 is a flow diagram showing a process performed by the facility in some embodiments in order to handle a drug ordering request on behalf of a CDC.

FIG. 15 is a flow diagram showing a process performed by the facility in some embodiments in order to handle a drug ordering request on behalf of a CDC. In act 1501, the facility receives a request that includes the identity of a drug to be ordered and a quantity of that drug to be ordered. In some embodiments, the request received in act 1501 is automatically generated, such as based upon current CDC inventory levels for the drug, current inventory levels for the drug among member hospitals, actual and anticipated demand for the drug by member hospitals, etc.

In acts 1502-1504, the facility loops through each member hospital of the CDC. In act 1503, the facility determines the lowest cost for the hospital to order a quantity of the requested drug. The facility does so based upon the unapplied inpatient and outpatient dispenses by this hospital, in view of this hospital's prior ordering history for this drug from each supplier. In some embodiments, the facility performs act 1603 in accordance with the process shown in FIG. 2. In act 1504, if one or more additional member hospitals remain, then the facility continues in act 1502 to process the next hospital, else the facility continues in act 1505.

The facility repeats acts 1505-1510 until the order quantity specified by the request received in act 1501 is fully allocated across the member hospitals. In act 1506, the facility selects the hospital having the lowest cost. In act 1507, the facility adds a container of the requested drug to a draft order for the hospital selected in act 1506. In act 1508, the facility attributes dispenses by the selected hospital to the order, and accordingly reduces the selected hospital's tally of unapplied dispenses. In act 1509, the facility updates the lowest cost for the selected hospital to consider the selected hospital's tally of unapplied dispenses as reduced in act 1508. In act 1510, if the requested order quantity is not yet fully allocated across the member hospitals, then the facility continues in act 1505, else the facility continues in act 1511. In act 1511, the facility submits to suppliers the one or more orders constructed in act 1506. After act 1511, this process concludes.

Figure 16:
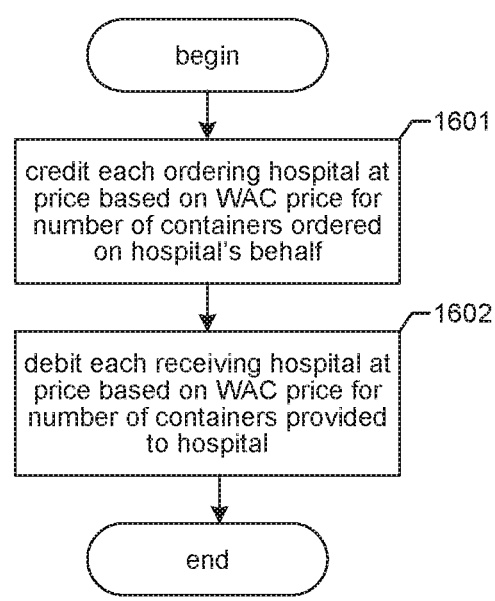
FIG. 16 is a flow diagram showing a process performed by the facility in some embodiments to manage payments among a CDC and its member hospitals for drugs ordered at the 340B price level.

FIG. 16 is a flow diagram showing a process performed by the facility in some embodiments to manage payments among a CDC and its member hospitals for drugs ordered at the 340B price level. When a CDC selects a particular member hospital to order a container of drugs at the 340B price level, this ordering hospital is charged the 340B price. In act 1601, the facility credits each ordering hospital at a price that is based on the WAC price level for the number of containers ordered by the CDC on the hospital's behalf. In some embodiments, the price based on the WAC price level used by the facility in act 1601 is the WAC price itself; in some embodiments, this price is a price that is marked down from the WAC price in order to compensate the CDC for its services on behalf of the member hospitals. By paying the ordering hospital at a price that is higher than the 340B price paid by the ordering hospital to the supplier, the CDC compensates the ordering hospital for the CDC's use of the ordering hospital's discounted 340B purchasing opportunity.

In act 1602, the facility debits each receiving hospital that will receive the order drugs at a price that is based on the WAC price level. In some embodiments, the price based on the WAC price level used by the facility in act 1602 is the WAC price itself; in some embodiments, this price is a price that is marked up from the WAC price in order to compensate the CDC for its services on behalf of the member hospitals.

In various embodiments, the credits and debits performed by the facility in acts 1601 and 1602 actually cause money to be transferred to and from the accounts of hospital members or their operators; update virtual account records that are later used as a basis to transfer money or issue invoices and/or payment checks; etc.

After act 1602, this process concludes.

Figure 17:
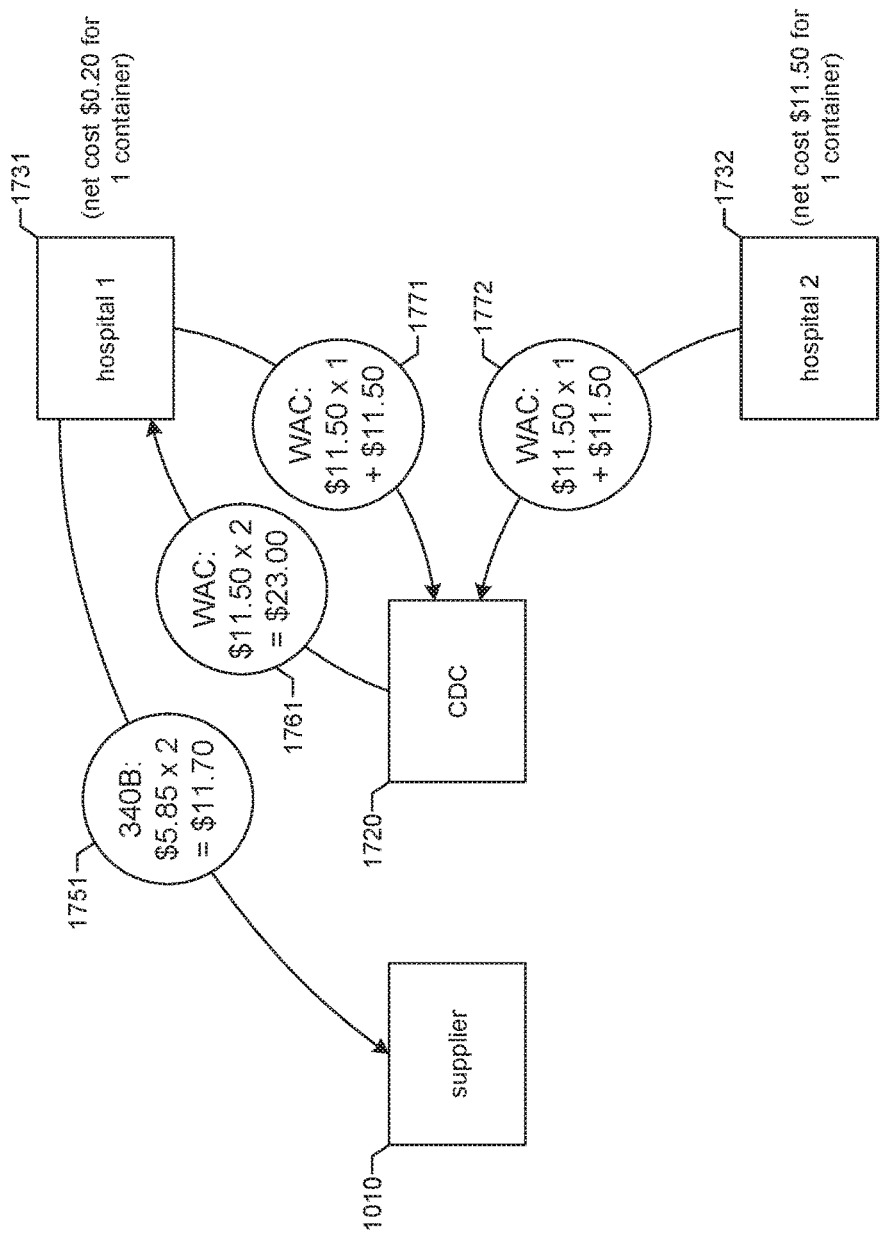
FIG. 17 is a diagram showing an example of accounting for a drug order placed by a CDC.

FIG. 17 is a diagram showing an example of accounting for a drug order placed by a CDC. The CDC 1720 places an order for two containers of a drug with supplier 1010 on behalf of a first hospital 1731. The order placed with the supplier is at the 340B price level for both containers, so the supplier charges 1751 the first hospital (the "ordering hospital") two times the 340B price of $5.85, $11.70 total. The CDC reimburses the first hospital for the order at the WAC price level by paying 1761 the first hospital two times the WAC price of $11.50, $23.00 total. In response to determining that one of the two containers will be distributed to the first hospital and the other of the two containers will be distributed to a second hospital 1732: the CDC charges the first hospital at the WAC price level of $11.50, $11.50 total; and the CDC similarly charges the second hospital at the WAC price level of $11.50, $11.50 total. Thus, the net cost to the first hospital for one container of the drug is $0.20, while the net cost to the second hospital for one container of the drug is $11.50. This lower net cost to the first hospital compensates the first hospital for the use of its 340B discounted purchasing opportunity.

U.S. patent application Ser. No. 16/178,446 filed on Nov. 1, 2018 is hereby incorporated by reference in its entirety. It will be appreciated by those skilled in the art that the above-described facility may be straightforwardly adapted or extended in various ways. While the foregoing description makes reference to particular embodiments, the scope of the invention is defined solely by the claims that follow and the elements recited therein.

I claim:

1. A method in a computing system for ordering a drug, comprising:

for each of a plurality of hospitals supplied with the drug via a Central Drug Distribution Center (CDC):
  maintaining, in a memory, a storage device, or both of the computing system:
    a first data structure comprising a plurality of entries, each entry corresponding to a dispense of a dose of a drug by that hospital, each entry comprising an indication of whether the dose was administered to an inpatient or an outpatient and a purchase ID of a purchase to which the dispense has been applied; and
    a second data structure comprising a plurality of entries, each entry corresponding to a seller price of a drug for that hospital at an undiscounted per-dose price, an inpatient discounted per-dose price, and an outpatient discounted per-dose price;
  determining a quantity of the drug and a container size that should be obtained for distribution through the CDC;
  in response to the determination:
    for each of the plurality of hospitals:
      (a) identifying a first seller from the second data structure having a lowest undiscounted per-dose price at which the drug is available to the hospital;
      (b) determining an inpatient dispense count and an outpatient dispense count based on contents of the first data structure, the inpatient dispense count indicating a number of doses of the drug administered to inpatients, the outpatient dispense count indicating a number of doses of the drug administered to outpatients;
      (c) where the hospital's inpatient dispense count is at least equal to the container size in which the drug is available:
        identifying a second seller from the second data structure having a lowest inpatient discounted per-dose price at which the drug is available to the hospital;
      (d) where the hospital's outpatient dispense count is at least equal to the container size in which the drug is available:
        identifying a third seller from the second data structure having a lowest outpatient discounted per-dose price at which the drug is available to the hospital and from which the drug has previously been purchased in the container size at the undiscounted per-dose price; and (e) selecting, among the first seller, the second seller, and the third seller, a seller having the lowest per-dose price for the determined container size at which the drug is available to the hospital;

initializing an empty set of planned orders for the drug;

until the determined quantity is fully allocated across the plurality of hospitals, repeating the following steps (f) through (i):

(f) selecting a hospital whose seller has the lowest per-dose price the selecting based in part on a corresponding dispense count of the selected hospital;

(g) adding to the set of planned orders a planned order to purchase a container of the drug of the container size from the seller of the selected hospital;

(h) decrementing the corresponding dispense count of the selected hospital by the container size; and (i) repeating steps (a) through (e) for the selected hospital to re-select the lowest per-dose price for the determined container size at which the drug is available to the selected hospital; and causing each of the planned orders of the set to be submitted to the corresponding seller.

2. The method of claim 1, further comprising:

for each submitted order, updating the first data structure for the hospital to whose seller the order was submitted, wherein updating the first data structure comprises:

where the submitted order is an order at an inpatient discounted price, setting the purchase IDs of a number of entries that correspond to the container size to a new purchase ID assigned to the order, each of the entries corresponding to a dispense of the drug to an inpatient; and where the submitted order is an order at an outpatient discounted price, setting the purchase IDs of the number of entries that corresponds to the container size to a new purchase ID assigned to the order, each of the entries corresponding to a dispense of the drug to an outpatient.

3. A non-transitory computer-readable medium having contents adapted to cause a computing system to perform a method, the method comprising:

for each of a plurality of medical facilities served by a Central Drug Distribution Center (CDC), maintaining in a memory, a storage device, or both of the computing System a first data structure comprising a plurality of entries, each entry corresponding to a dispense of a dose of a drug by that medical facility, each entry comprising an indication whether the dose was administered to an inpatient or an outpatient and a purchase ID of a purchase to which the dispense has been applied, and a second data structure comprising a plurality of entries, each entry corresponding to a supplier price of a drug for that medical facility at an undiscounted per-dose price, an inpatient discounted per-dose price, and an outpatient discounted per-dose price;

in response to determining that a distinguished quantity of a distinguished drug should be obtained for distribution through the CDC:

identifying, based on the contents of the second data structure, a lowest cost for the distinguished quantity of the distinguished drug offered to any of the plurality of medical facilities served by the CDC by any supplier of a plurality of suppliers among, for each of the plurality of medical facilities:

the undiscounted price level;

where a value of a first counter indicating doses of the distinguished drug administered by the medical facility to inpatients that have not been used as a basis for reordering the distinguished drug at a discounted inpatient price level is at least equal to the distinguished quantity, the discounted inpatient price level; and where a value of a second counter indicating doses of the distinguished drug administered by the medical facility to outpatients that have not been used as a basis for reordering the distinguished drug at a discounted outpatient price level is at least equal to the distinguished quantity, the discounted outpatient price level;

wherein the values of the first counter and the second counters are determined based on contents of the first data structure; and ordering the distinguished quantity of the distinguished drug from a supplier of the plurality of suppliers corresponding to the identified cost at the price level corresponding to the identified cost on behalf of the medical facility to which the distinguished drug is offered at the identified cost.

4. The non-transitory computer-readable medium of claim 3, the method further comprising:

where the distinguished drug is ordered at the discounted outpatient price level, updating the first data structure for the medical facility on behalf of which the distinguished drug was ordered, updating the first data structure comprising setting the purchase IDs of a number of entries that correspond to the distinguished quantity to a new purchase ID assigned to the order, each of the entries corresponding to a dispense of the distinguished drug to an outpatient.

5. The non-transitory computer-readable medium of claim 4, the method further comprising:

where the distinguished drug is ordered at the discounted inpatient price level, updating the first data structure for the medical facility on behalf of which the distinguished drug was ordered, updating the first data structure comprising setting the purchase IDs of the number of entries that correspond to the distinguished quantity to a new purchase ID assigned to the order, each of the entries corresponding to a dispense of the distinguished drug to an inpatient.

6. A computing system, comprising:

at least one processor; and a memory having contents adapted to cause the computing system to, when the contents are executed by the at least one processor, perform a method, the method comprising:

for a plurality of medical facilities served by a Central Drug Distribution Center (CDC), maintaining in the memory of the computing system a first data structure comprising a plurality of entries, each entry corresponding to a dispense of a dose of a drug by that medical facility, each entry comprising an indication whether the dose was administered to an inpatient or an outpatient and a purchase ID of a purchase to which the dispense has been applied and a second data structure comprising a plurality of entries, each entry corresponding to a supplier price of a drug for that medical facility at an undiscounted per-dose price, an inpatient discounted per-dose price, and an outpatient discounted per-dose price;

in response to determining that a distinguished quantity of a distinguished drug should be obtained for distribution through the CDC:
  identifying the lowest cost, based on the contents of the second data structure, for the distinguished quantity of the distinguished drug offered to any of the plurality of medical facilities served by the CDC by any supplier of a plurality of suppliers among, for each of the plurality of medical facilities:
    the undiscounted price level;
    where a value of a first counter indicating doses of the distinguished drug administered by the medical facility to inpatients that have not been used as a basis for reordering the distinguished drug at a discounted inpatient price level is at least equal to the distinguished quantity, the discounted inpatient price level; and
    where a value of a second counter indicating doses of the distinguished drug administered by the medical facility to outpatients that have not been used as a basis for reordering the distinguished drug at a discounted outpatient price level is at least equal to the distinguished quantity, the discounted outpatient price level;
  wherein the values of the first counter and the second counters are determined based on contents of the first data structure; and
  ordering the distinguished quantity of the distinguished drug from a supplier of the plurality of suppliers corresponding to the identified cost at the price level corresponding to the identified cost on behalf of the medical facility to which the distinguished drug is offered at the identified cost.

7. The computing system of claim 6, the method further comprising:
  where the distinguished drug is ordered at the discounted outpatient price level, updating the first data structure for the medical facility on behalf of which the distinguished drug was ordered, updating the first data structure comprising setting the purchase IDs of a number of entries that corresponds to the distinguished quantity to a new purchase ID assigned to the order, each of the entries corresponding to a dispense of the distinguished drug to an outpatient.

8. The computing system of claim 6, the method further comprising:
  where the distinguished drug is ordered at the discounted inpatient price level, updating the first data structure for the medical facility on behalf of which the distinguished drug was ordered, updating the first data structure comprising setting the purchase IDs of a number of entries that corresponds to the distinguished quantity to a new purchase ID assigned to the order, each of the entries corresponding to a dispense of the distinguished drug to an inpatient.

* * * * *